(12) United States Patent
Salzbrenner

(10) Patent No.: US 11,043,293 B1
(45) Date of Patent: Jun. 22, 2021

(54) HEALTHCARE PROVIDER INTERFACE FOR TREATMENT OPTION AND AUTHORIZATION

(71) Applicant: The Board of Regents of the University of Nebraska, Lincoln, NE (US)

(72) Inventor: Stephen Salzbrenner, Omaha, NE (US)

(73) Assignee: Board of Regents of the University of Nebraska, Lincoln, NE (US)

(*) Notice: Subject to any disclaimer, the term of this patent is extended or adjusted under 35 U.S.C. 154(b) by 53 days.

(21) Appl. No.: 16/212,236

(22) Filed: Dec. 6, 2018

Related U.S. Application Data

(60) Provisional application No. 62/595,742, filed on Dec. 7, 2017.

(51) Int. Cl.
  *G16H 20/10* (2018.01)
  *G06Q 40/08* (2012.01)
  *G06F 3/0484* (2013.01)
  *G06F 3/0482* (2013.01)
  *G06F 3/0483* (2013.01)
  (Continued)

(52) U.S. Cl.
  CPC .......... *G16H 20/10* (2018.01); *G06F 3/0482* (2013.01); *G06F 3/0483* (2013.01); *G06F 3/0484* (2013.01); *G06Q 10/10* (2013.01); *G06Q 40/08* (2013.01); *G16H 10/60* (2018.01)

(58) Field of Classification Search
  CPC ........ G16H 20/10; G16H 20/13; G16H 20/17; G16H 10/60; G16H 10/20; G06H 20/10; G06H 20/13; G06H 20/17; G06F 3/0482; G06F 3/0483; G06F 3/0484; G06Q 10/10; G06Q 40/08
  See application file for complete search history.

(56) References Cited

U.S. PATENT DOCUMENTS 8,799,018 B1 * 8/2014 Rea ................ G16H 70/40
  705/2
10,296,715 B1  5/2019 Smith et al.
10,742,654 B1  8/2020 Pinsonneault et al.
(Continued)

OTHER PUBLICATIONS

"Pros and Cons of Step Therapy". CaliforniaHealthline [online], [retrieved on Feb. 26, 2021], Retrieved from the Internet (URL: https://californiahealthline.org/news/pros-and-cons-of-step-therapy/), 2013 (Year: 2013).*

*Primary Examiner* — Daniel Samwel
(74) *Attorney, Agent, or Firm* — Nasr Patent Law LLC; Faisal K. Abou-Nasr

(57) ABSTRACT

A healthcare provider user interface for treatment option and authorization is disclosed herein. In embodiments, a healthcare provider device includes a display coupled to one or more processors. The display includes a graphical user interface comprising one or more input interface display pages and one or more output interface display pages. The one or more input interface display pages may include one or more input boxes configured to receive information including patient physiological information, insurance provider information, historical medication prescriptions, and one or more medical diagnoses. The one or more output interface display pages may include a medication list generated based on the received information and a prior authorization form configured to receive one or more prior authorization input fields.

16 Claims, 11 Drawing Sheets

(51) Int. Cl.
*G16H 10/60* (2018.01)
*G06Q 10/10* (2012.01)

(56) References Cited

U.S. PATENT DOCUMENTS

| | | | |
|---|---|---|---|
| 2003/0069760 A1* | 4/2003 | Gelber | G06Q 40/08 705/4 |
| 2005/0015278 A1* | 1/2005 | Ghouri | G06Q 10/10 705/2 |
| 2006/0235280 A1* | 10/2006 | Vonk | G06F 19/3481 600/300 |
| 2009/0198518 A1* | 8/2009 | McKenzie | G16H 10/00 705/3 |
| 2009/0228302 A1* | 9/2009 | Rothschild | G16H 40/67 705/3 |
| 2010/0088108 A1* | 4/2010 | Machado | G06F 16/284 705/2 |
| 2012/0179481 A1* | 7/2012 | Patel | G06Q 30/02 705/2 |
| 2013/0179177 A1 | 7/2013 | Dhavle et al. | |
| 2014/0244288 A1* | 8/2014 | Goodman | G06Q 10/10 705/2 |
| 2015/0120319 A1* | 4/2015 | Wilson | G16H 50/20 705/2 |
| 2015/0142463 A1* | 5/2015 | Vinals | G06Q 30/0627 705/2 |
| 2015/0278474 A1* | 10/2015 | Stueckemann | G06F 19/3456 705/2 |
| 2016/0055314 A1 | 2/2016 | Anderson et al. | |
| 2016/0094681 A1* | 3/2016 | Wu | G06F 16/211 709/203 |
| 2016/0188820 A1 | 6/2016 | Brown et al. | |
| 2016/0260003 A1* | 9/2016 | Hill | G06K 19/06028 |
| 2016/0358279 A1* | 12/2016 | Ghouri | G16H 15/00 |
| 2017/0083681 A1* | 3/2017 | Sprintz | G16H 20/10 |
| 2018/0046763 A1* | 2/2018 | Price, Jr. | G16H 10/60 |
| 2018/0082030 A1* | 3/2018 | Allen | G16H 10/20 |
| 2018/0233228 A1* | 8/2018 | Ungab | A61B 5/7275 |
| 2018/0324186 A1* | 11/2018 | Dintenfass | H04L 63/04 |

* cited by examiner

HEALTHCARE PROVIDER INTERFACE FOR TREATMENT OPTION AND AUTHORIZATION

CROSS-REFERENCE TO RELATED APPLICATION

The present application claims the benefit under 35 U.S.C. § 119(e) of U.S. Provisional Application Ser. No. 62/595,742, filed Dec. 7, 2017, entitled TREATMENT OPTION AND AUTHORIZATION SYSTEM AND METHOD, naming Stephen Salzbrenner as inventor, which is incorporated herein by reference in the entirety.

BACKGROUND

Health insurance practices are evolving, requiring time-consuming prior authorization (PA) for many procedures and medications. It is estimated that physicians and their support staff spend approximately 10-20 hours a week handling prior authorization matters. This process is complicated by the fact that prescribers often do not know which medications will require prior authorization when selecting treatments or medications for patients. Furthermore, approximately one third of medication prescriptions which require prior authorization are abandoned, resulting in sick, untreated patients. Some current systems utilize electronic prior authorization procedures (ePA procedures). However, even with ePA procedures, 64% of patients must wait a day for the prior authorization to be approved, with roughly 30% of patients having to wait for longer than a day. Furthermore, current ePA procedures often are not tailored to specific patients, and often result in patients receiving medical care which is not optimal for their specific needs.

SUMMARY

A healthcare provider user interface for treatment option and authorization is disclosed herein. In embodiments, a healthcare provider device includes a display coupled to one or more processors. The display includes a graphical user interface comprising one or more input interface display pages and one or more output interface display pages. The one or more input interface display pages may include one or more input boxes configured to receive information including patient physiological information, insurance provider information, historical medication prescriptions, and one or more medical diagnoses. The one or more output interface display pages may include a medication list generated based on the received information and a prior authorization form configured to receive one or more prior authorization input fields.

A system for processing a prior authorization or medication request claim is also disclosed herein. In embodiments, the system includes a server and a healthcare provider device. The healthcare provider device includes a display coupled to one or more processors. The display includes a graphical user interface comprising one or more input interface display pages configured to receive input information for transmission to the server and one or more output interface display pages generated by the server based on received input information. The one or more input interface display pages may include one or more input boxes configured to receive information including patient physiological information, insurance provider information, historical medication prescriptions, and one or more medical diagnoses. The one or more output interface display pages may include a medication list generated based on the received information and a prior authorization form configured to receive one or more prior authorization input fields.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION

Reference will now be made in detail to the subject matter disclosed, which is illustrated in the accompanying drawings. The present disclosure is particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

As noted previously herein, prior authorization (PA) is frequently required by insurance providers for many procedures and medications. It is estimated that physicians and their support staff spend approximately 10-20 hours a week handling prior authorization matters, causing prior authorization matters to be rated as a "high or extremely high" burden by 75% of physicians in 2017. Even with electronic prior authorization (ePA) systems and methods, patients often have to wait a day or more for their medical treatments and/or medications to be approved, resulting in abandoned medications and sick, untreated patients.

Referring generally to FIGS. 1 through 3H, embodiments of the present disclosure are directed to a healthcare provider user interface device (e.g., healthcare provider device 102) having a specially configured graphical user interface (GUI) that streamlines the process of obtaining prior authorization for medications and treatment. Embodiments of the present disclosure are also directed to a system and method that employ the healthcare provider device. It is contemplated herein that the configuration of the healthcare provider device may provide for faster and more efficient prior authorization procedures.

Figure 1:
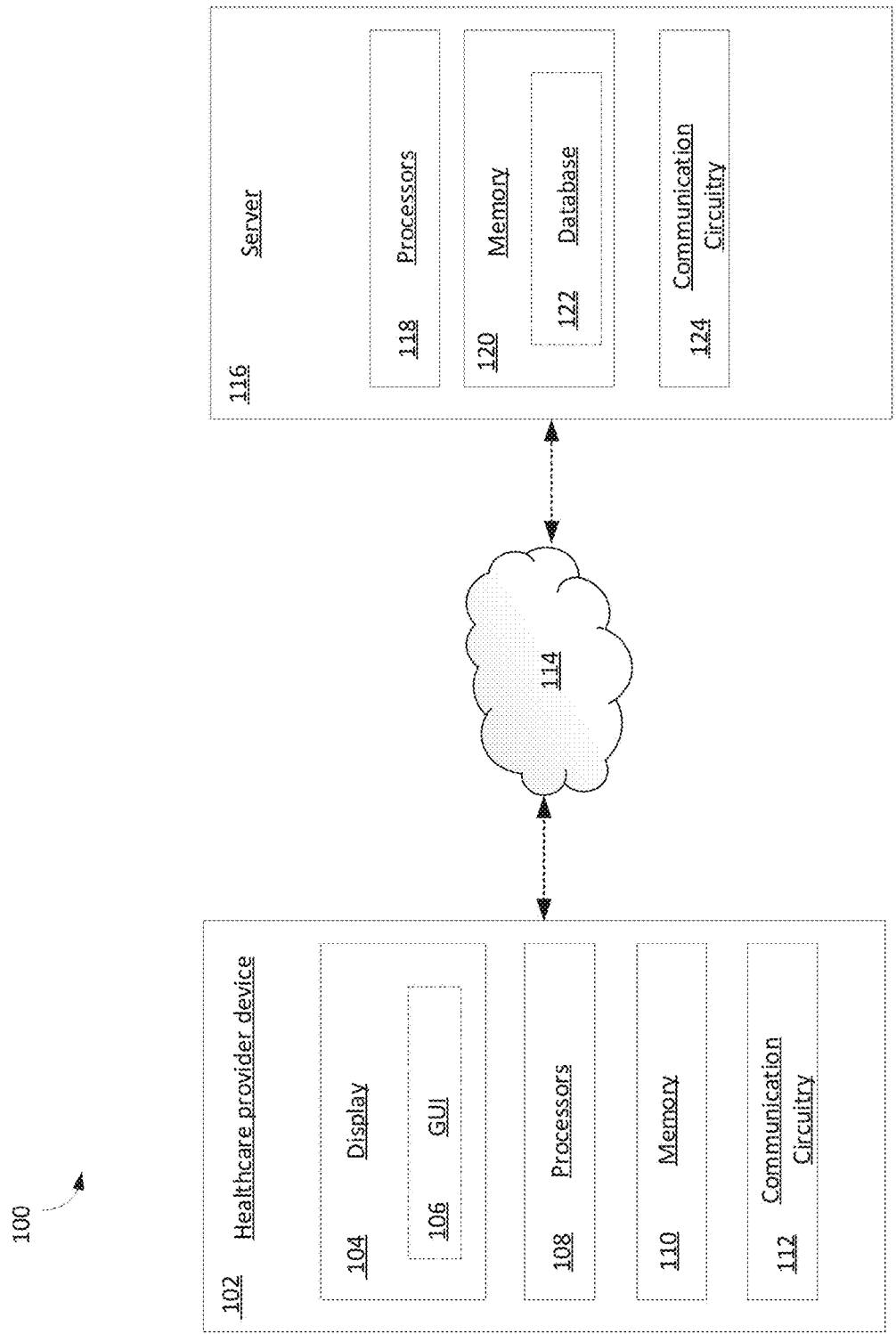
FIG. 1 is a block diagram illustrating a system that employs a healthcare provider interface, in accordance with one or more embodiments of the present disclosure.

FIG. 1 illustrates a system 100 including a healthcare provider device 102, a network 114, and a server 116. In embodiments, the healthcare provider device 102 may include a display 104 with a specially configured GUI 106, one or more processors 108, a memory 110, and communication circuitry 112. The healthcare provider device 102 may include a wide range of user interface devices known in the art. For example, the healthcare provider device 102 may include a cell phone, a smart phone, a smart watch, a tablet, a desktop computer, or the like. It is noted herein that the specific configuration of the healthcare provider device 102, and, more specifically, the display 104 of the healthcare provider device 102, may enable patients and medical care providers to more effectively and efficiently obtain prior authorization for medical treatments and/or medications. For the purposes of the present disclosure, it is noted herein that the terms "graphical user interface" (e.g., GUI 106) and "healthcare user interface" may be used interchangeably, unless noted otherwise herein.

The healthcare provider device 102 includes a display 104 used to display data of the system 100 to a user (e.g., patient, healthcare provider, or the like). The display 104 of the healthcare provider device 102 may include any display known in the art. For example, the display may include a CRT display, a liquid crystal display (LCD), a light-emitting diode (LED) display, an organic light-emitting diode (OLED) based display, or the like. Those skilled in the art should recognize that any display device capable of integration with a healthcare provider device 102 is suitable for implementation in the present disclosure. In embodiments, the display 104 may include a GUI 106. It is contemplated herein that a user may input selections and/or instructions responsive to data displayed to the user via the GUI 106.

In embodiments, the healthcare provider device 102 may include a GUI 106 generated at the display 104 by the one or more processors 108. In this regard, the one or more processors 108 may be configured to execute a set of program instructions stored in memory 110, wherein the set of program instructions are configured to cause the one or more processors 108 to carry out various steps of the present disclosure.

In some embodiments, the healthcare provider device 102 includes communication circuitry 112. The communication circuitry 112 may include any circuitry and/or network interface configured for interfacing the healthcare provider device 102 with the network 114. For example, the communication circuitry 112 may include wireline-based interface devices (e.g., DSL-based interconnection, cable-based interconnection, T9-based interconnection, or the like). By way of another example, the communication circuitry 112 may include a wireless-based interface device employing GSM, GPRS, CDMA, EV-DO, EDGE, WiMAX, 3G, 4G, 4G LTE, 5G, WiFi protocols, RF, LoRa, or the like.

The healthcare provider device 102 may be configured to transmit and/or receive data to/from the server 116 via the network 114. The network 114 may include any network known in the art for communicatively coupling hardware (e.g., healthcare provider device 102) to a server 116. In this regard, the network 114 may include the internet. By way of another example, the network 114 may include a cellular network configured to transmit data. By way of another example, the network 114 may include a cloud-based architecture.

In embodiments, the server 116 may include one or more processors 116, a memory 120 including one or more databases 122, and communication circuitry 124. It is contemplated herein that the server 116 may include any server hosted remotely with respect to the healthcare provider device 102. In additional and/or alternative embodiments, the server 116 may be proximate to the healthcare provider device 102. The communication circuitry 124 of server 114 may include any circuitry and/or network interface configured for interfacing the server 116 with the network 114. For example, the communication circuitry 124 may include wireline-based interface devices (e.g., DSL-based interconnection, cable-based interconnection, T9-based interconnection, or the like). By way of another example, the communication circuitry 124 may include a wireless-based interface device employing GSM, GPRS, CDMA, EV-DO, EDGE, WiMAX, 3G, 4G, 4G LTE, 5G, WiFi protocols, RF, LoRa, or the like. Accordingly, server 116 may be configured to send and receive data with the healthcare provider device 102 via network 114.

The one or more processors 118 of server 116 may be configured to execute a set of program instructions stored in memory 120, wherein the set of program instructions are configured to cause the one or more processors 118 to generate the GUI 106 at the display 104 and to carry out various steps of the present disclosure. It is noted herein that various steps or processes of the present disclosure may be described as being carried out by the one or more processors 108 of healthcare provider device 102 and/or the one or more processors 118 of the server 116. However, these descriptions are not to be regarded as limiting. In this regard, various steps or processes of the present disclosure may be carried out by either of the one or more processors 108, 118, unless noted otherwise herein.

In embodiments, the memory 120 may include one or more databases 122.

The one or more databases 122 may include any databases associated with healthcare information, insurance provider information, healthcare provider information, patient health records, or the like. For example, the one or more databases 122 may include, but are not limited to, patient medical history databases, prescription drug monitoring programs (PDMP), or the like. By way of another example, the one or more databases 122 may include state or national online health information exchange databases. For instance, the one or more databases 122 may include a database of the Nebraska Health Information Institute (NeHII) or other state sponsored medical programs.

It is noted herein that the one or more components of system 100 may be communicatively coupled to the various other components of system 100 in any manner known in the art. For example, the healthcare provider device 102 and server 116 may be communicatively coupled to each other and other components via a wireline (e.g., copper wire, fiber optic cable, or the like) or wireless connection (e.g., RF coupling, IR coupling, data network communication (e.g., WiFi, WiMax, Bluetooth and the like).

In embodiments, the one or more processors 108, 118 may include any one or more processing elements known in the art. In this sense, the one or more processors 108, 118 may include any microprocessor-type device configured to execute software algorithms and/or instructions. For example, the one or more processors 108, 118 may consist of a desktop computer, mainframe computer system, workstation, image computer, parallel processor, or other computer system (e.g., networked computer) configured to execute a program configured to operate the system 100, as described throughout the present disclosure. It should be recognized that the steps described throughout the present disclosure may be carried out by a single computer system or, alternatively, multiple computer systems. Furthermore, it should be recognized that the steps described throughout the present disclosure may be carried out on any one or more of the one or more processors 108, 118. In general, the term "processor" may be broadly defined to encompass any device having one or more processing elements, which execute program instructions from memory 110, 120. Therefore, the above description should not be interpreted as a limitation on the present disclosure but merely an illustration.

The memory 110, 120 may include any storage medium known in the art suitable for storing program instructions executable by the associated one or more processors 108, 118 and the data received from the sub-systems of system 100 (e.g., healthcare provider device 102, server 116, or the like). For example, the memory 110, 120 may include a non-transitory memory medium. For instance, the memory 110, 120 may include, but is not limited to, a read-only memory (ROM), a random-access memory (RAM), a magnetic or optical memory device (e.g., disk), a magnetic tape, a solid-state drive, or any combination thereof. It is further noted that memory 110, 120 may be housed in a common controller housing with the one or more processors 108, 118. In some embodiments, the memory 110, 120 may be located remotely with respect to the physical location of the processors 108, 118, and healthcare provider device 102, server 116, or the like. In embodiments, the memory 110, 120 maintains program instructions for causing the one or more processors 108, 118 to carry out the various steps described through the present disclosure.

In embodiments, the healthcare provider device 102 includes a GUI 106 generated at the display 104 by the one or more processors 108. For example, the program instructions may be configured to cause the one or more processors 108 to generate a GUI 106 at the display 104, the GUI 106 including one or more input interface display pages 300, 320, 320, 330, 340. The one or more processors 108 may be further configured to store information input into healthcare provider device 102 via the one or more input interface display pages 300, 310, 320, 330, 340 in memory 110. In additional embodiments, the one or more processors 108 may be configured to transmit one or more signals to server 116 via network 114, wherein the one or more signals are configured to cause the one or more processors 118 of server 116 to retrieve information from the memory 120 and/or one or more databases 122. The one or more processors 108 may be configured to retrieve information stored in one or more databases of memory 110. In other embodiments, the one or more processors 108 may be communicatively coupled to one or more additional components of healthcare provider device 102 including, but not limited to, one or more microphones, one or more speakers, one or more cameras, one or more chip readers, or any combination thereof. The steps performed by the one or more processors 108 will be discussed in greater detail herein with reference being made to FIGS. 2A-2B.

Figure 2A:
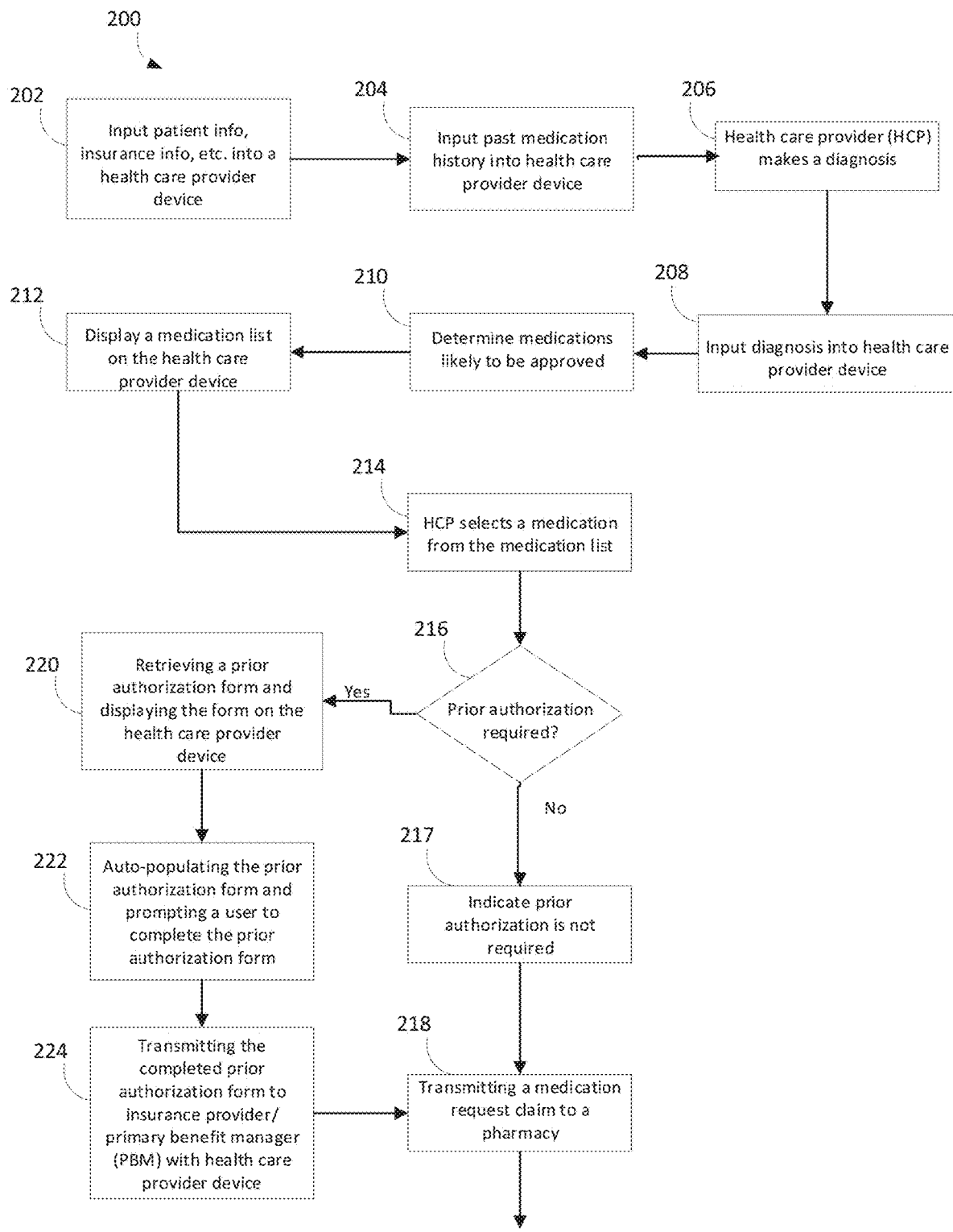
FIG. 2A is a flow diagram illustrating a portion of a method that employs a healthcare provider interface, in accordance with one or more embodiments of the present disclosure.
Figure 2B:
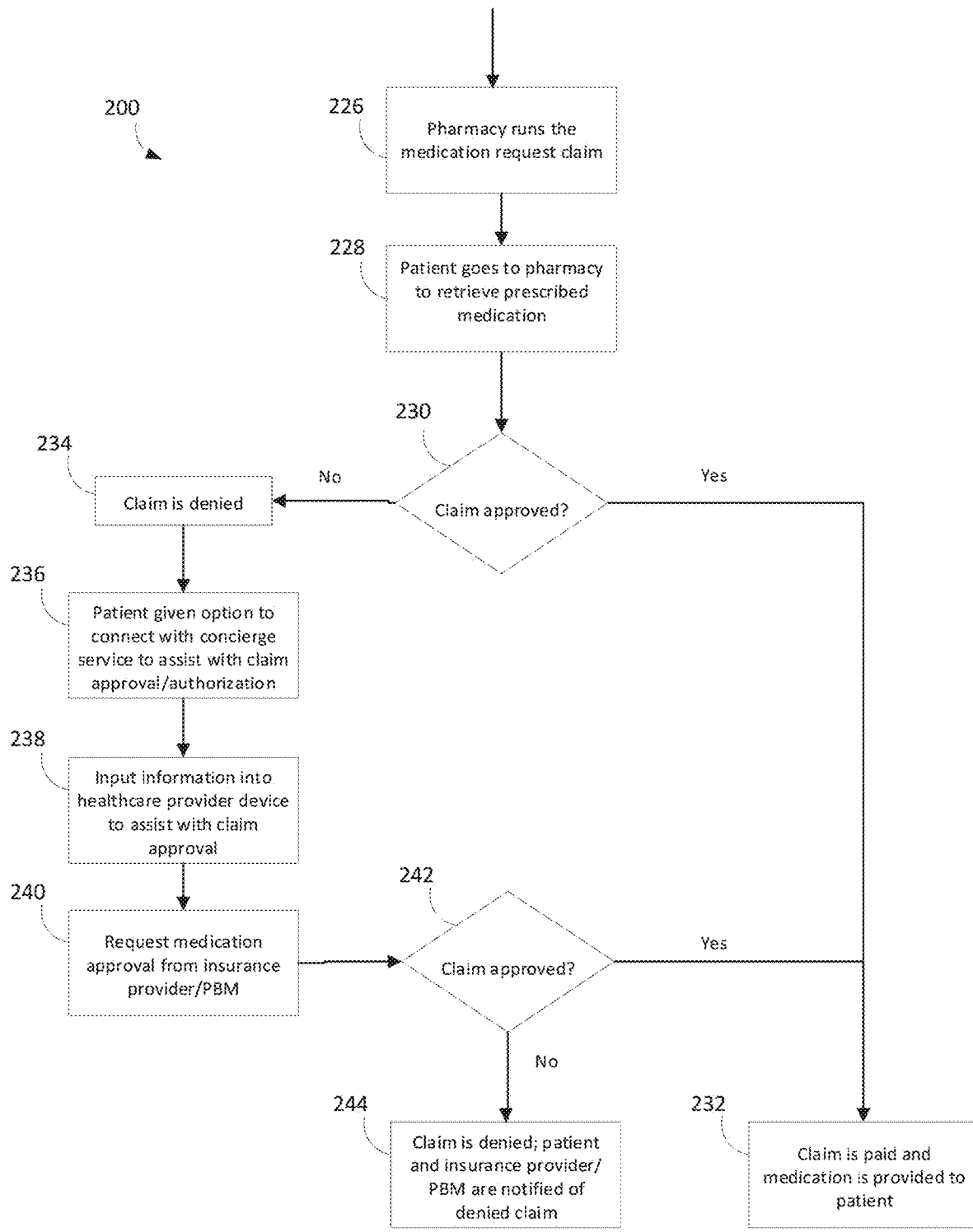
FIG. 2B is a flow diagram illustrating a portion of a method that employs a healthcare provider interface, in accordance with one or more embodiments of the present disclosure.

FIGS. 2A-2B illustrate a method 200 for using a healthcare provider device 102, in accordance with one or more embodiments of the present disclosure. Accordingly, the method 200 may be shown and described as being implemented by healthcare provider device 102 of system 100, as depicted in FIG. 1. It is noted herein that the steps of method 200 may be implemented all or in part by system 100. It is further recognized, however, that the method 200 may not be limited to the system 100 in that additional or alternative system-level embodiments may carry out all or part of the steps of method 200.

Furthermore, it may be appreciated herein that the steps of method 200 depicted in FIGS. 2A-2B are enabled by the configuration of the healthcare provider device 102. More specifically, system 100 and the method 200 are enabled by the input/output interface display pages of the GUI 106 generated at the display 104 of the healthcare provider device 102, as illustrated in FIGS. 3A-3G.

Figure 3A:
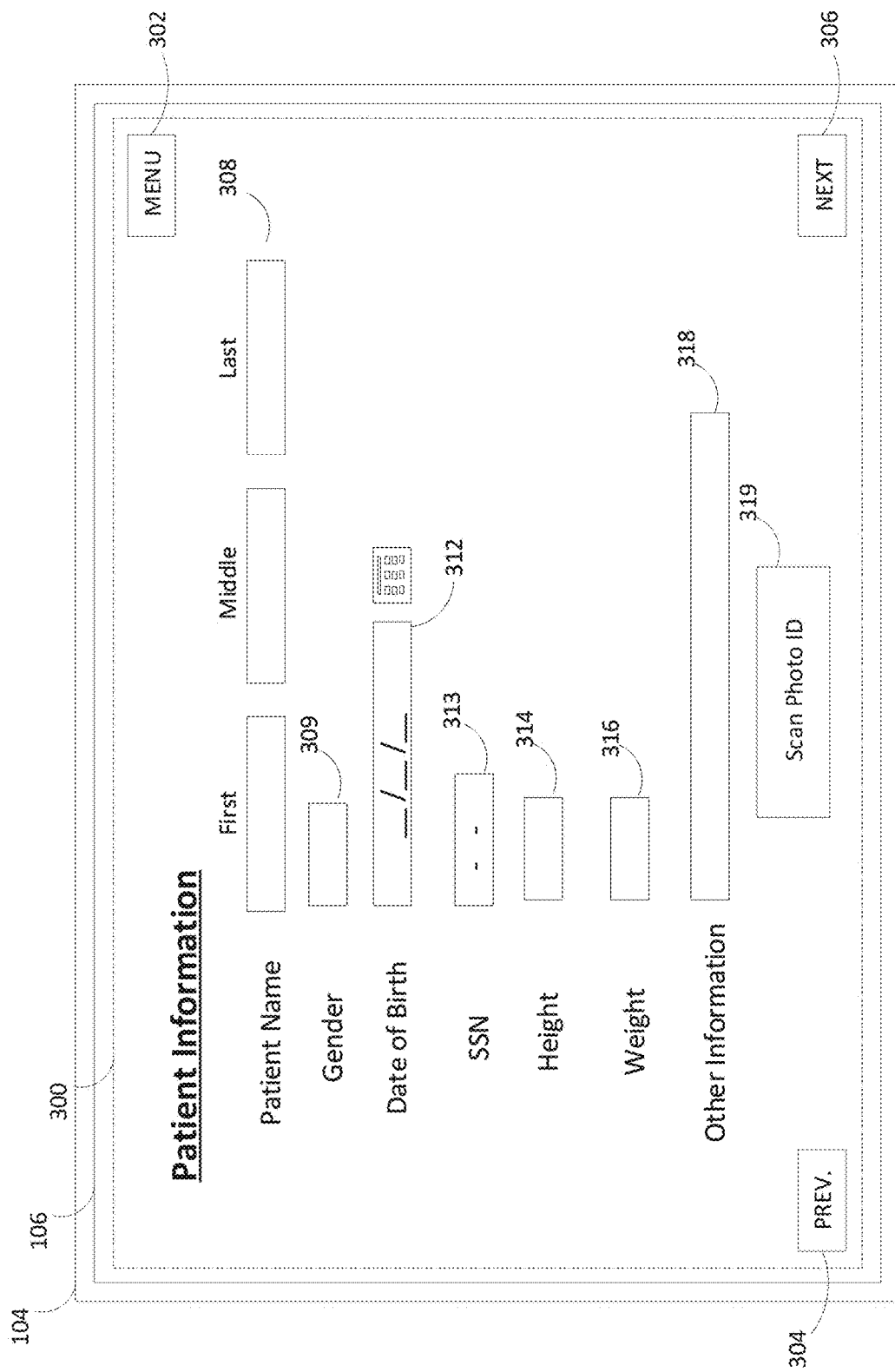
FIG. 3A illustrates an input interface display page of a healthcare provider interface depicting input boxes for receiving patient information, in accordance with one or more embodiments of the present disclosure.

In a step 202, a patient may input personal information via the GUI 106 of the healthcare provider device 102. For example, FIG. 3A illustrates an input interface display page 300 of a GUI 106 generated at a display 104 of a healthcare provider device 102 depicting input boxes for receiving patient information, in accordance with one or more embodiments of the present disclosure. As shown in FIG. 3A, input interface display page 300 may include, but is not limited to, one or more input boxes 308 configured to receive the name of the patient, an input box 309 configured to receive a gender of the patient, an input box 312 configured to receive the date of birth and/or age of the patient, an input box 313 configured to receive a social security number (SSN) of the patient, an input box 314 configured to receive the height of the patient, an input box 316 configured to receive the weight of the patient, an input box 318 configured to receive other information regarding the patient, or any combination thereof.

In additional and/or alternative embodiments, input interface display page 300 may include a button 319 configured to cause the healthcare provider device 102 to scan a photo ID of the patient. In this regard, button 319 may be configured to cause the healthcare provider device 102 to access a scanning or imaging device (e.g., camera, chip reader, bar code scanner, or the like) and/or optical recognition software in order to retrieve patient information from a photo ID. It is contemplated herein that information retrieved from scanning a photo ID may be used to auto-populate the input boxes 308-318.

As used throughout the present disclosure, the term "input box" may be used to refer to a structure of the display 104 which is configured to receive information. Furthermore, the term "input box" is used throughout the present disclosure to refer to various structures located on the GUI 106 of the display 104 with which a user (e.g., patient, healthcare provider, or the like), may interact. The term "input box" may include, but is not limited to, one or more plain text input boxes, auto-fill input text boxes, drop-down input boxes, drop-down selectable/searchable lists, predictive text input boxes, or any combination thereof. In embodiments with drop-down input boxes or selectable lists, selectable entries and/or predictive selectable options may be stored in memory 110 such that the drop-down input boxes or selectable lists may be updated in real time or substantially real time as a user inputs information. For the purposes of the present disclosure, the term "select" or "selecting" may be regarded as any action known in the art for selecting including, but not limited to, clicking, pressing, touching, hovering, or the like.

In embodiments, input box 318 may be configured to receive additional patient information regarding the patient's medical history and/or condition. Additional patient information may include any information which may be valuable in assessing a patient's medical condition, prescribing a course of medical treatment, prescribing medication, or the like. For example, additional patient information may include patient biologic information including, but not limited to, one or more genetic profile characteristics of the patient. The one or more processors 108 may be configured to store information/data input via input interface display page 300 in memory 110.

It is noted herein that healthcare provider device 102 may include a device dedicated solely for healthcare provider use and handling prior authorization matters. In an alternative embodiment, healthcare provider device 102 may include a patient's smartphone. For example, a personal smartphone may include an application ("app") with input/output interface display pages 300, 310, 320, 330, 340, 350, 360 illustrated in FIGS. 3A-3G.

In embodiments, input interface display page 300 depicted in FIG. 3A includes a button 302 configured to cause the display 104 of the healthcare provider device 102 to display a menu. In other embodiments, input interface display page 300 includes a first button 304 and a second button 306 configured to toggle between input/output interface display pages 300, 310, 320, 330, 340, 350, 360 illustrated in FIGS. 3A-3G. Additional and/or alternative embodiments are illustrated in FIG. 3H.

Figure 3B:
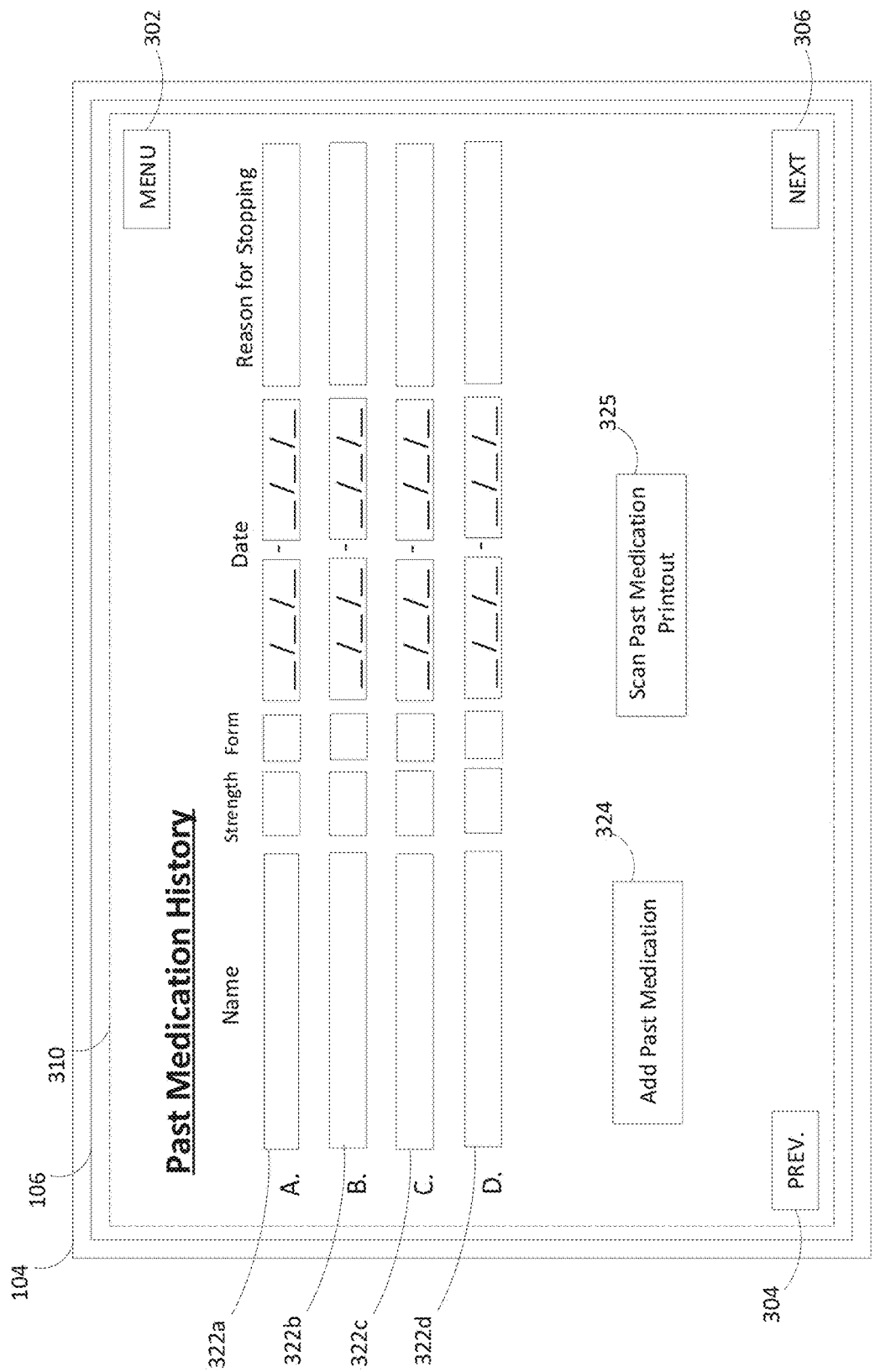
FIG. 3B illustrates an input interface display page of a healthcare provider interface depicting input boxes for receiving past medication history information of a patient, in accordance with one or more embodiments of the present disclosure.
Figure 3C:
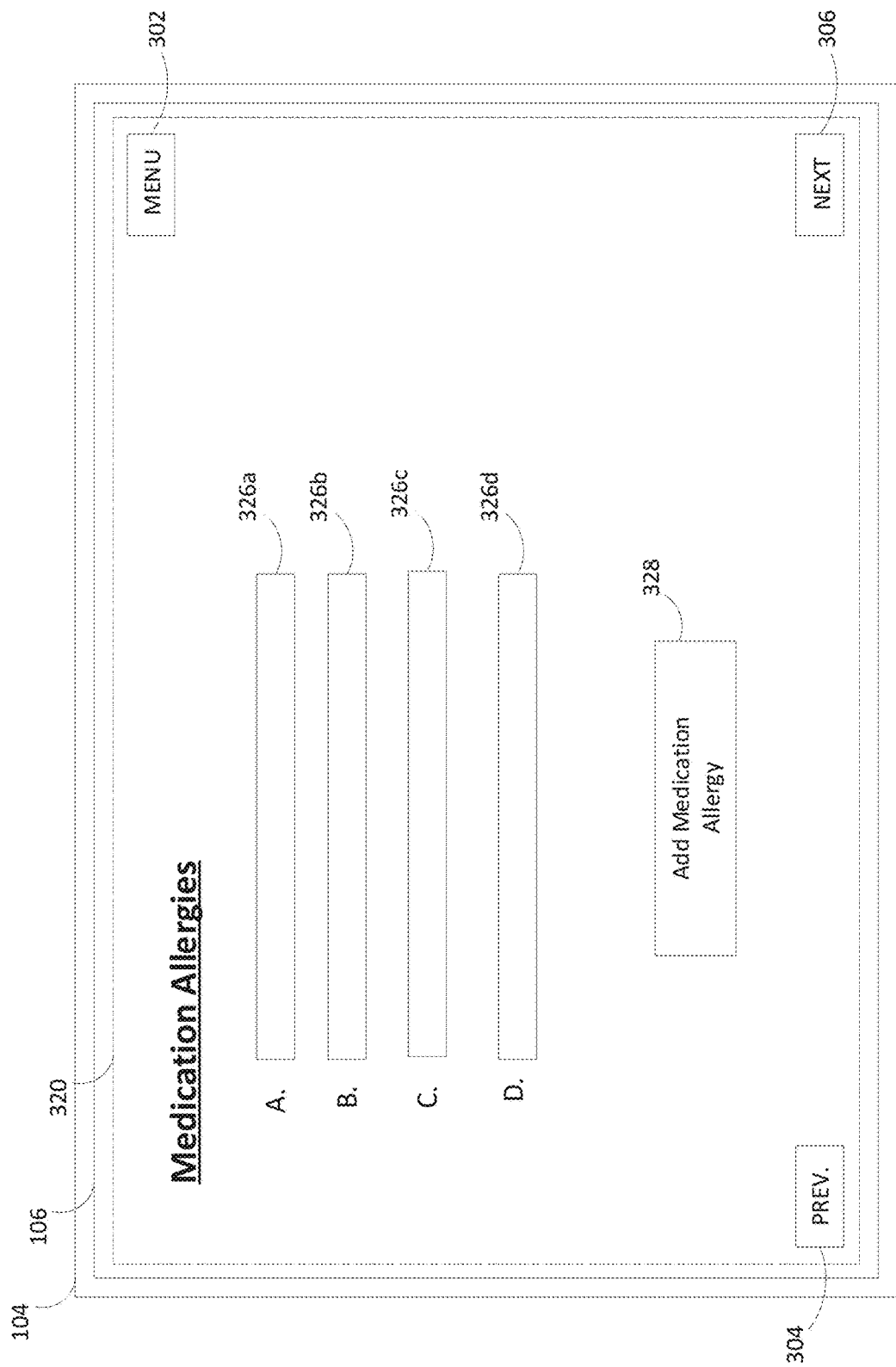
FIG. 3C illustrates an input interface display page of a healthcare provider interface depicting input boxes for receiving medication allergies of a patient, in accordance with one or more embodiments of the present disclosure.
Figure 3D:
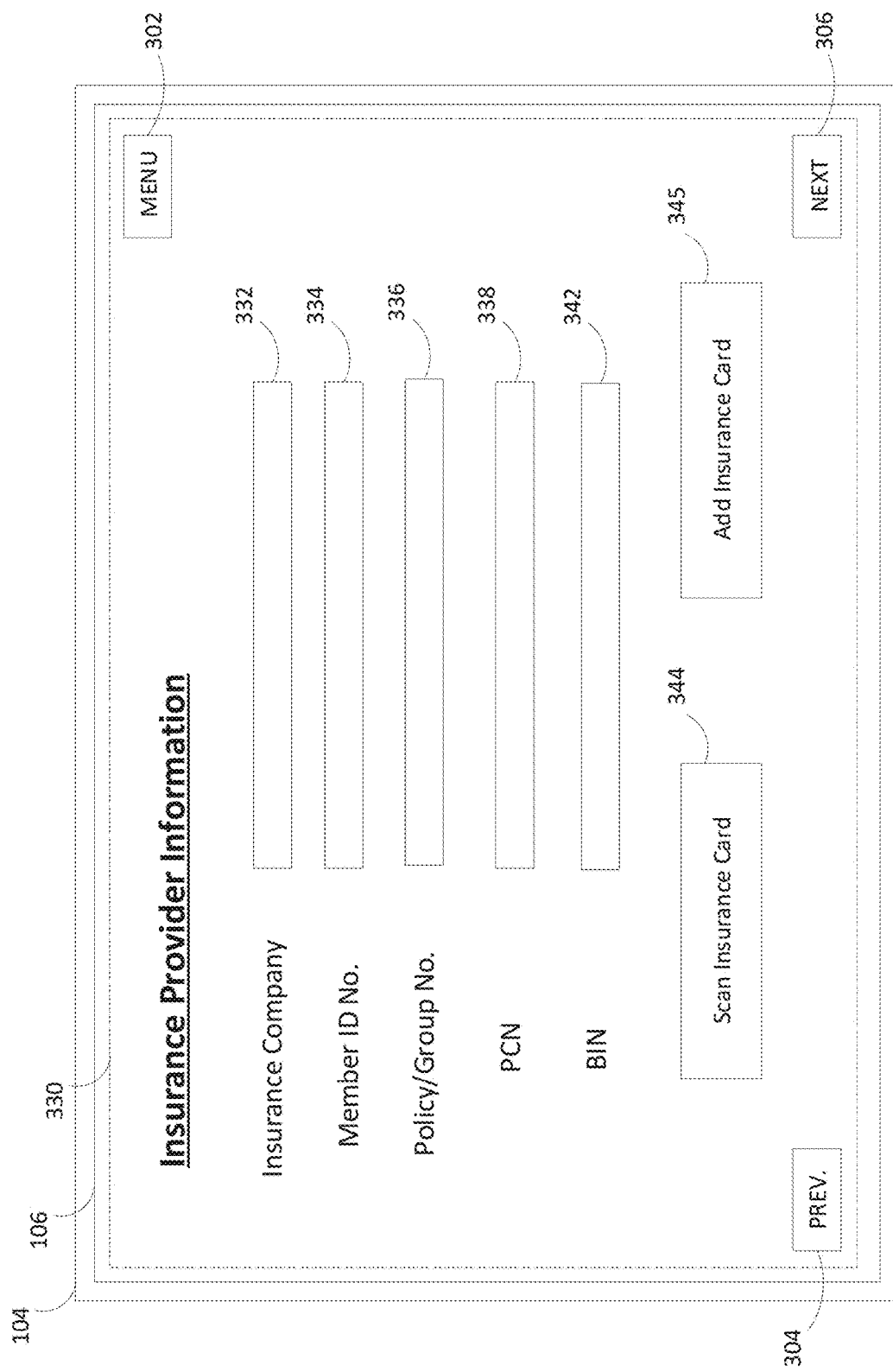
FIG. 3D illustrates an input interface display page of a healthcare provider interface depicting input boxes for receiving insurance provider information, in accordance with one or more embodiments of the present disclosure.
Figure 3E:
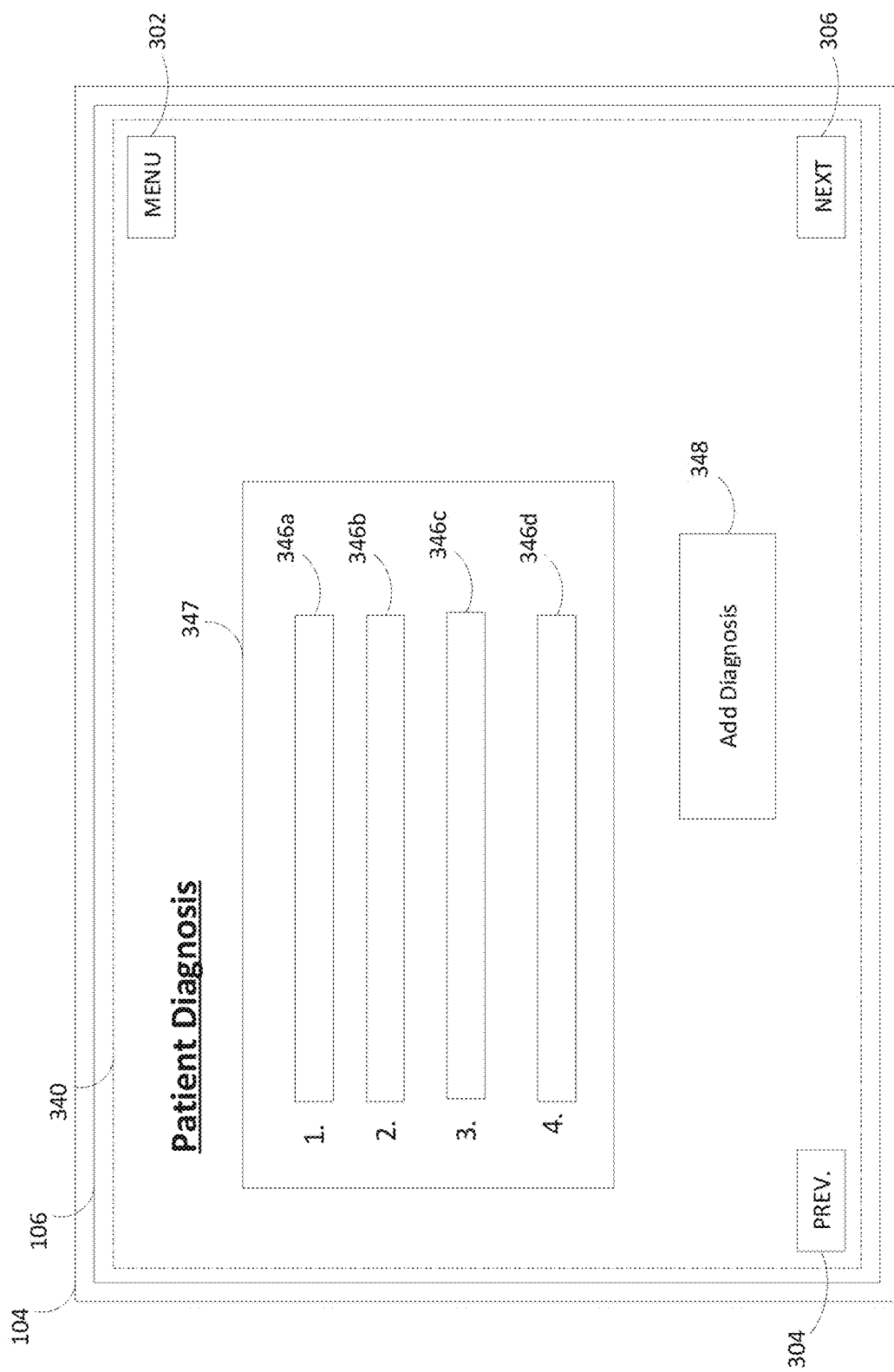
FIG. 3E illustrates an input interface display page of a healthcare provider interface depicting input boxes for receiving a patient diagnosis, in accordance with one or more embodiments of the present disclosure.
Figure 3F:
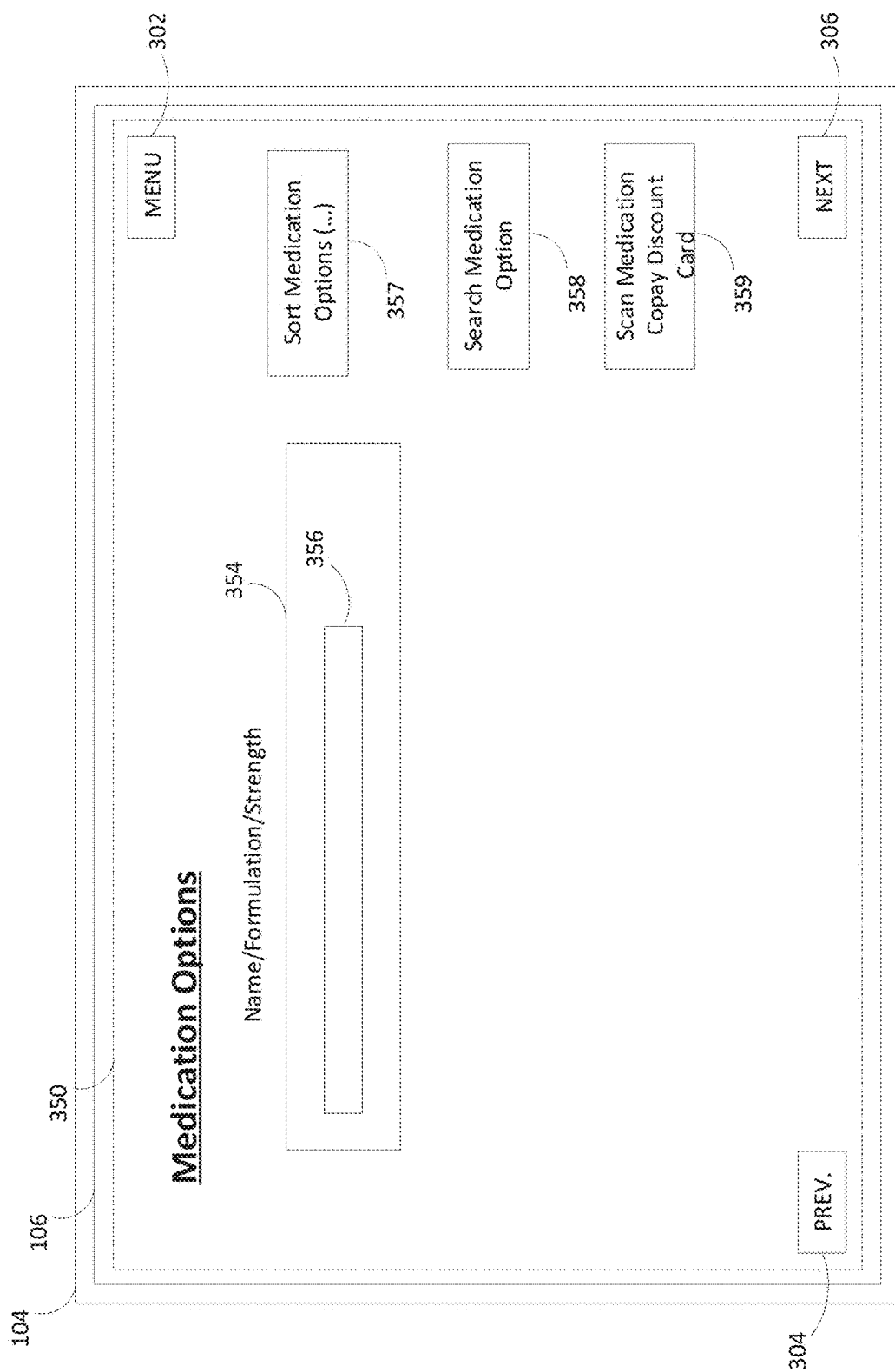
FIG. 3F illustrates an output interface display page of a healthcare provider interface depicting a list of medication options, in accordance with one or more embodiments of the present disclosure.
Figure 3G:
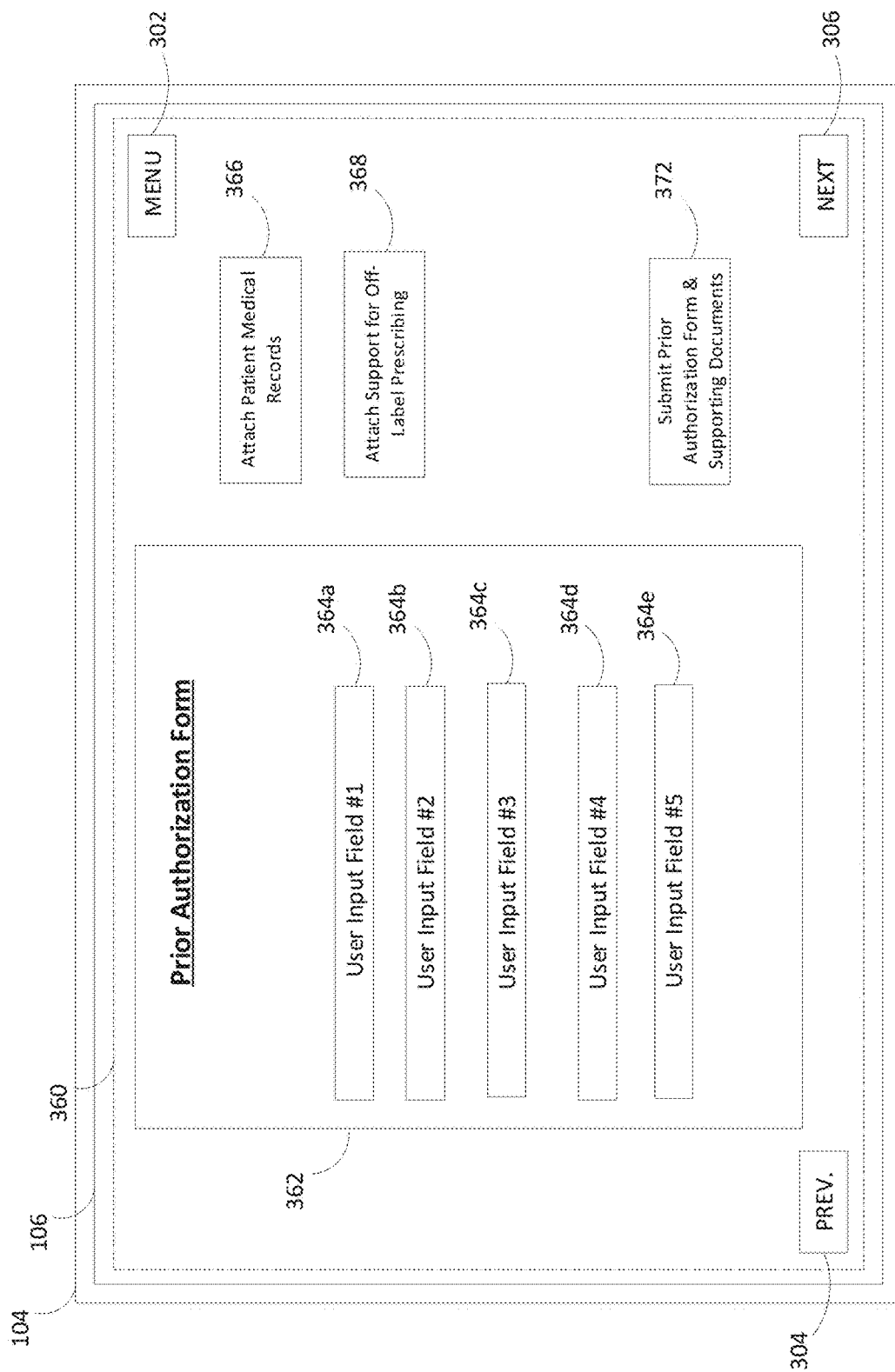
FIG. 3G illustrates an output interface display page of a healthcare provider interface depicting a prior authorization form, in accordance with one or more embodiments of the present disclosure.
Figure 3H:
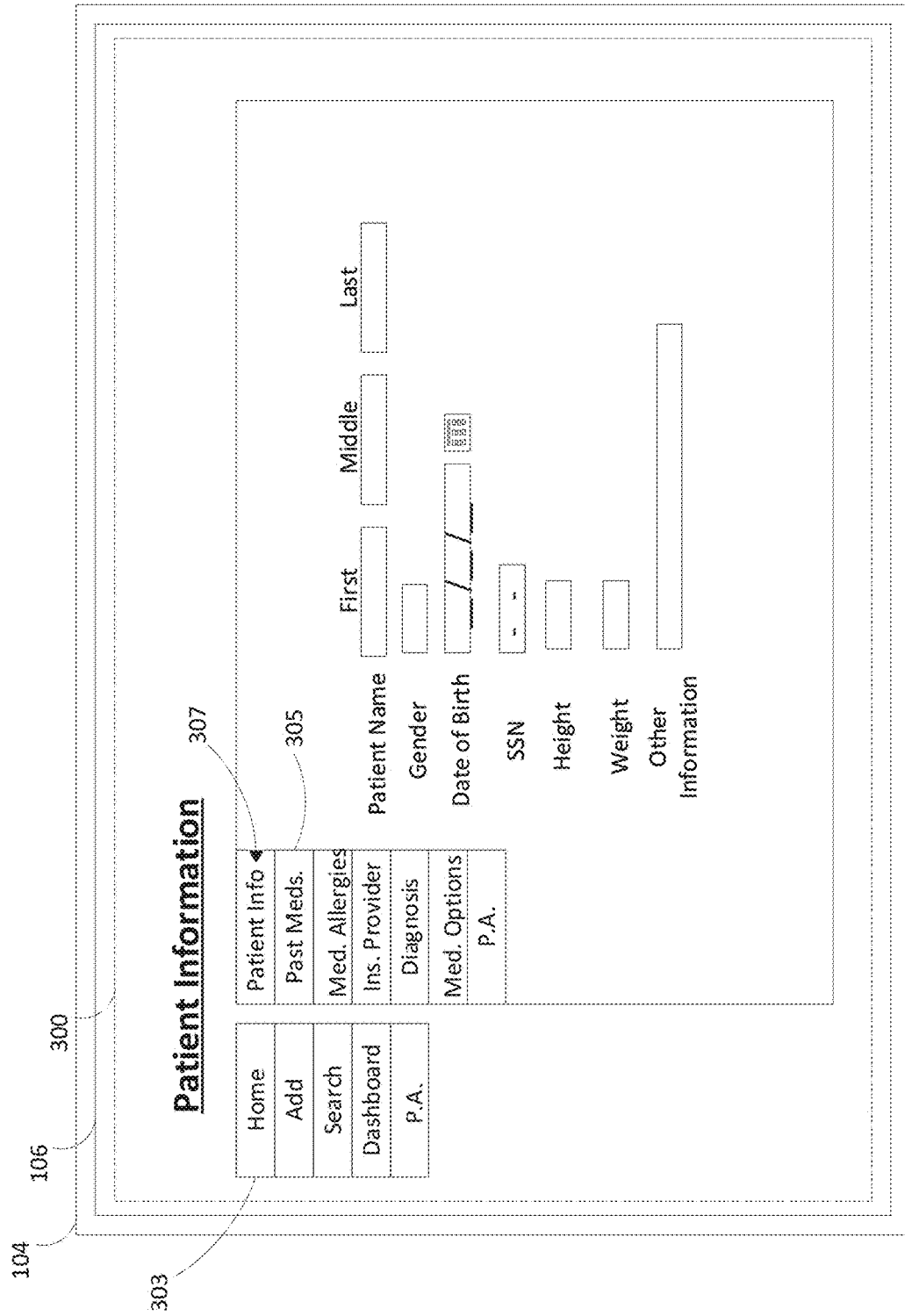
FIG. 3H illustrates an input interface display page of a healthcare provider interface depicting input boxes for receiving patient information, in accordance with one or more embodiments of the present disclosure.

FIG. 3H illustrates an input interface display page 300 of a GUI 106 generated at a display 104 of a healthcare provider device 102 depicting input boxes for receiving patient information, in accordance with one or more embodiments of the present disclosure. As shown in FIG. 3H, input interface display page 300 may include, but is not limited to, a main menu 303 including one or more buttons, and a navigation pane 305 including one or more buttons. It is noted herein that the main menu 303 and/or the navigation pane 305 may be used in addition to or in lieu of the buttons 302, 304, 306 illustrated in FIG. 3A. It is noted herein that the one or more buttons of the main menu 303 and the one or more buttons of the navigation pane 305 may be configured to cause the healthcare provider device 102 to display one or more of the input interface display pages or one or more of the output interface display pages. In this regard, it is contemplated herein that the one or more buttons of the navigation pane 305 may correspond to the input interface display pages and the output interface display pages. In embodiments, an indicator 307 may be configured to indicate which input interface display page or output interface display page is displayed on the healthcare provider device 102. It is further noted herein that the main menu 303 and/or the navigation pane 305 may be incorporated into any of the input interface display pages or output interface display pages of the present disclosure.

It is noted herein that any of the steps of the present disclosure may include storing time-stamped information in memory 110. For example, it is contemplated herein that information inputted into the healthcare provider device 102 may be time-stamped such that the precise time information was input is saved along with the inputted information. Furthermore, it is contemplated herein the identity of the individual inputting information may be important. In this regard, it is contemplated herein that identifying information associated with the individual inputting information into healthcare provider device 102 may be stored in memory 110. For example, the healthcare provider device 102 may include various "profiles" or other "user accounts" in which individuals (e.g., healthcare providers, doctors, nurses, and the like) may "sign in" or otherwise indicate their identity. For instance, a nurse may "sign in" to a healthcare provider device 102 such that any information input while the nurse is signed in is stored in memory 110 as being input by the nurse. Similarly, the nurse may "sign out," and a doctor may subsequently sign in such that any information input while the doctor is signed in is stored in memory 110 as being input by the doctor. It is contemplated that the identity of individuals inputting information may be determined using any method known in the art including, but not limited to, profiles, biometric data (e.g., retinal scans, fingerprint scans, and the like), passwords, pass codes, and the like.

In a step 204, past medication history of the patient is input into the healthcare provider device 102. For example, FIG. 3B illustrates an input interface display page 310 of a GUI 106 generated at display 104 of a healthcare provider device 102 depicting input box groups 322 for receiving past medication history information (e.g., step therapy information) of a patient, in accordance with one or more embodiments of the present disclosure. To the extent applicable, the description associated with structures illustrated in FIG. 3A may be regarded as applying to structures illustrated in FIG. 3B, unless noted otherwise herein.

As shown in FIG. 3B, input interface display page 310 may include one or more input boxes (e.g., input box groups 322a, 322b, 322c, 322d) configured to receive past medication history information (e.g., step therapy information) of a patient. Past medication history information of a patient may include, for example, the name of a medication, the strength, the form (e.g., capsule, tablet, and the like) the start and stop dates that the medication was used (e.g., date range), and a reason for stopping the medication. Past medication information may also be input in the form of SIG codes. In this regard, the one or more input box groups 322a, 322b, 322c, 322d may comprise multiple input boxes for each past medication entry. For example, as shown in FIG. 3B, each past medication entry may include a separate input box for the name of the medication, strength, form, date, and reason for stopping, such that input box group 322a comprises five separate input boxes. It is contemplated herein that input boxes configured to receive information associated with a reason for stopping a medication may include selectable drop-down menus, selectable predictive text drop-down menus, and the like.

In embodiments, input box groups 322a, 322b, 322c, 322d may include, but are not limited to, plain text input boxes, auto-fill input text boxes, drop-down input boxes, drop-down selectable/searchable lists, or the like. For example, as a user inputs the name of a medication in an input box of the input box group 322a, the input box may expand to include a list of predictive selectable options generated based on the information previously input into input box. The predictive selectable options may be stored in memory 110. By way of another example, input box of the input box group 322a may predictively auto-fill the names of medications based on information previously input into input box.

In some embodiments, input interface display page 310 may include a button 324 configured to add an input box group 322 configured to receive past medication entries. For example, referring to FIG. 3B, if a user input four past medication entries, the user may select the button 324 to add one or more additional input box groups 322 configured to receive one or more additional past medication entries.

In additional and/or alternative embodiments, the past medication history of a patient may be retrieved from one or more databases 122 of server 116. In this regard, past medication history may be auto-filled into input interface display page 310 based on information received from the one or more databases 122 of server 116. For example, the one or more processors 108 may transmit signals via network 114 to server 116, which may cause the one or more processors 118 to retrieve a patient's medical history from the one or more databases 122 stored on memory 120. Continuing with the same example, the one or more processors 118 may transmit medical history information retrieved from the one or more databases 122 to the healthcare provider device 102 via network 114. As noted previously herein, the one or more processors 118 may be configured to retrieve information from any medical information database known in the art including, but not limited to, patient medical history databases, prescription drug monitoring programs (PDMP), state or national online health information exchange databases (e.g., NeHII), or any combination thereof. If past medication history information is auto-filled from information retrieved from the one or more databases 122, a user may be able to edit and/or supplement auto-filled information with button 324.

In another embodiment, input interface display page 310 may include a button 325 configured to allow a user to scan a past medication printout. It is noted herein that the ability to scan a past medication printout may allow for a more effective and efficient entry of past medication prescriptions. Accordingly, in additional and/or alternative embodiments, healthcare provider device 102 may include and/or be communicatively coupled to a scanning or imaging device including, but not limited to, a camera, a bar code scanner, a QR code scanner, a chip reader, or the like. Furthermore, it is contemplated herein that the healthcare provider device 102 may be configured to execute optical character recognition (OCR) software or other programs which are configured to convert typed or handwritten text into computer readable text. Text scanned and translated by then be auto-filled into the one or more input box groups 322.

In embodiments, a user (e.g., healthcare provider, patient, or the like) may be able to input medicinal allergies of the patient. For example, FIG. 3C illustrates an input interface display page 320 of a GUI 106 generated at a display 104 of a healthcare provider device 102 depicting input boxes for receiving medication allergies of a patient, in accordance with one or more embodiments of the present disclosure. To the extent applicable, description associated with structures illustrated in FIGS. 3A-3B may be regarded as applying to structures illustrated in FIG. 3C, unless noted otherwise herein.

As shown in FIG. 3C, input interface display page 320 may include one or more input boxes 326a, 326b, 326c, 326d configured to receive medication allergies of the patient. In embodiments, input boxes 326a, 326b, 326c, 326d may include, but are not limited to, plain text input boxes, auto-fill input text boxes, drop-down input boxes, drop-down selectable/searchable lists, or the like. In embodiments, input interface display page 320 may include a button 328 configured to add an input box 326 configured to receive medication allergy information.

FIG. 3D illustrates an input interface display page 330 of a GUI 106 generated at a display 104 of a healthcare provider device 102 depicting input boxes for receiving insurance provider information, in accordance with one or more embodiments of the present disclosure. To the extent applicable, description associated with structures illustrated in FIGS. 3A-3C may be regarded as applying to structures illustrated in FIG. 3D, unless noted otherwise herein.

As shown in FIG. 3D, input interface display page 330 may include one or more input boxes configured to receive insurance provider information. In this regard, input interface display page 330 may include, but is not limited to, an input box 332 configured to receive the name of an insurance provider (e.g., insurance company), an input box 334 configured to receive a member ID number, an input box 336 configured to receive a policy and/or group number, an input box 338 configured to receive a primary care network (PCN) number, an input box 342 configured to receive a bank identification number (BIN), or any combination thereof.

In embodiments, input interface display page 330 may include a button 344 which may be selected to scan a patient's insurance provider card. Accordingly, in additional and/or alternative embodiments, healthcare provider device 102 may include and/or be communicatively coupled to a scanning or imaging device including, but not limited to, a camera, a bar code scanner, a QR code scanner, a chip reader, or the like. For example, upon selection of button 344, the one or more processors 108 of healthcare provider device 102 may be configured to access a camera of the healthcare provider device 102 which may be used to take an image of the patient's insurance card. After taking the picture, the set of program instructions in memory 110 may be configured to cause the one or more processors 108 to inspect the image and extract insurance provider information from the image. The one or more processors 108 may then be further configured to auto-fill the input boxes of input interface display page 320 with the information extracted from the image of the insurance card. By way of another example, upon selection of button 344, the one or more processors 108 of the healthcare provider device 102 may be configured to cause a chip reader of the healthcare provider device 102 to search and scan a chip of an insurance card. In other embodiments, input interface display page 330 may include a button 345 configured to add an additional insurance card.

In a step 206, a healthcare provider (HCP) makes a diagnosis of the patient. In a step 208, the diagnosis made by the HCP is input into the healthcare provider device 102. FIG. 3E illustrates an input interface display page 300 of a GUI 106 generated at a display 104 of a healthcare provider device depicting input boxes for receiving a patient diagnosis, in accordance with one or more embodiments of the present disclosure. To the extent applicable, description associated with structures illustrated in FIGS. 3A-3D may be regarded as applying to structures illustrated in FIG. 3E, unless noted otherwise herein.

As shown in FIG. 3E, input interface display page 340 may include a diagnosis list 347 including one or more input boxes 346a-346d configured to receive a medical diagnosis from the healthcare provider. In embodiments, input boxes 346a-346d, may include, but are not limited to, plain text input boxes, auto-fill input text boxes, drop-down input boxes, drop-down selectable/searchable lists, or the like. For example, as a user (e.g., health care provider) begins to input a diagnosis into input box 326a input box 346a and/or input box 346b may expand to display selectable and/or searchable diagnoses denoted with ICD-10 codes which may be predicted by the one or more processors 108 based on information input into the input boxes 346a Upon entering an ICD-10 code into input box 346a, input box 346b may auto-fill with the corresponding plain text description of the ICD-10 diagnosis. It is further contemplated that, upon selection and/or entry of a diagnosis description in input box 346a input box 346a may auto-fill with the corresponding ICD-10 code. In embodiments, input interface display page 340 may include a button 348 configured to add an additional diagnosis input box 346 when the button 348 is selected.

In other embodiments, information input into the GUI 106 of the healthcare provider device 102 via input interface display pages 300, 310, 320, 330, 340 may be stored in memory 110. Information stored in memory 110 may be stored such that input information is associated with a particular patient. For example, memory 110 may include a database which includes information input for one or more patients. In embodiments, the one or more processors 108 may be configured to transmit information input via input interface display pages 300, 310, 320, 330, 340 to the server 116 via network 114. It is contemplated herein that information transmitted to server 116 may be added to the memory 120 and/or the one or more databases 122. Information associated with a patient and transmitted to server 116 may further be used to filter searches/inquiries performed by the one or more processors 118 on the one or more databases 122.

In a step 210, a list of medications which are likely to be approved are determined. In a step 212, the medication list including one or more medication options is displayed by the healthcare provider device 102. For example, FIG. 3F illustrates an output interface display page 350 of a GUI 106 generated at a display 104 of a healthcare provider device 102 depicting a list of medication options, in accordance with one or more embodiments of the present disclosure. To the extent applicable, description associated with structures illustrated in FIGS. 3A-3E may be regarded as applying to structures illustrated in FIG. 3F, unless noted otherwise herein.

In embodiments, output interface display page 350 includes a medication list 354. The medication list 354 may include a drop-down scroll box 356 which lists each medication of the medication list 354. For example, the medication list 354 may include a drop-down, continuous scroll box 356 which may be sorted by any number of criteria including, but not limited to, medication cost, insurance provider prior authorization rules, and the like. In embodiments, the drop-down scroll box 356 may include a predictive text list, in which a user may be able to begin typing the name of a medication and the list automatically jumps to a medication within the list in response to a prediction made based on the inputted information.

Medications listed in the scroll box 356 may include any information associated with a medication option including, but not limited to, the name of the medication, the strength, the form, quantity limits, applicable SIG codes, and the like. The medication list 354 may include any number of medications within the scroll box 356. The medication list 354 may be generated based on a number of factors including, but not limited to, the inputted medical diagnosis (e.g., input box 346a, 346b), insurance provider formulary rules (e.g., rules specific to the insurance provider company and/or insurance plan provided in input box 332 and input box 334), insurance provider prior authorization rules, patient physiological information (e.g., height input box 314, weight input box 316, age input box 312, or the like), one or more step therapy prescriptions (e.g., historical medication prescriptions) (e.g., input box groups 322a, 322b, 322c, 322d), or any combination thereof. By way of another example, the medication list 354 may be generated by patient biologic information (e.g., genetic profile information input in input box 318, or the like).

It is contemplated herein that the medication list 354 may include highlighting, bolded text, asterisks, icons, or other methods known in the art to identify particular characteristics of the medications 356. Medication characteristics which may be highlighted or otherwise noted include, but are not limited to, medications which the patient has previously tried, medications which are known to require prior authorization, medications which may cause allergic reactions based on inputted allergy information, and the like. For example, medications which the patient has already tried may appear in blue text, whereas medications which are likely to cause allergic reactions for the patient may appear in red text. By way of another example, medications which require prior authorization may be denoted by highlighting, an asterisk, or bolded text. It is noted herein hat the examples provided are not to be regarded as limiting.

The output interface display page 350 may include a drop-down menu 357 configured to provide options for sorting the medications 356 of the medication list 354. In this regard, upon selection of the drop-down menu 357, the button 357 may expand into a drop-down menu including selectable filters configured to filter and/or sort the medication list 354 according to varying parameters or characteristics. Upon selection of a selectable filter provided by drop-down menu 357, the order of the medications 356 in the medication list 354 may be adjusted based upon the selected filter. The medications 356 of the medication list 354 may be sorted according to a number of factors including, but not limited to, medication cost, probability of approval by the insurance provider, patient preferences, patient ratings, insurance provider preferences, insurance provider ratings, availability, and genetic profile information of the patient, or any combination thereof.

In embodiments, the output interface display page 350 may include a button 358 configured to receive a medication option search inquiry. For example, a healthcare provider may know of a particular medication which may be applicable to the patient, but the medication may not appear in the medication list 354. Upon selection of button 358, the button 358 may expand into an input box configured to receive an input from the healthcare provider. The input box may include a plain text input box, an auto-fill input text box, a drop-down input box, drop-down selectable/searchable lists, a predictive text input box, or any combination thereof. After entering a medication option search via button 358, the medication list 354 may be configured to display the searched medication, or inform the healthcare provider that the searched medication does not appear within the medication list 354.

In embodiments, the output interface display page 350 may include a button 359 configured to cause the healthcare provider device 102 to scan a medication copay discount card. Accordingly, as noted otherwise herein, the healthcare provider device 102 may include a scanning or imaging device including, but not limited to, a camera, a bar code scanner, a QR code scanner, or the like. Furthermore, the healthcare provider device may be configured to execute optical character recognition (OCR) software. In an additional and/or alternative embodiment, button 359 may be configured to expand into an input box configured to receive a copay discount code. It is contemplated herein that entry of a valid copay discount may alter the price of one or more medications 356 within the medication list 354. In this regard, in embodiments where the medication list 354 is sorted according to factors including price, the entry of a valid copay discount may alter the arrangement of the medication list 354.

A healthcare provider may be able to select a medication 356a, 356b, 356c, 356d of the medication list 354 in order to view more information regarding the medication. For example, upon selecting or hovering over a medication 356, output interface display page 350 and/or a separate output interface display page may display details associated with the selected medication 356. Details associated with the selected medication 356 may include, but are not limited to, scientific and/or generic names, prescribing practices, primary purposes, side-effects, mechanisms of action, pharmacokinetics, medication interactions, black box warnings, monitoring requirements, dietary effects (e.g., food/drink reactions, and the like), or any combination thereof. For instance, upon selecting a medication 356, display 104 may display a separate output interface display page including a text box with conveying detailed information regarding the selected medication.

While output interface display page 350 is shown and described in terms of a list of medication options, this is not a limitation of the present disclosure, unless noted otherwise herein. In this regard, it is contemplated that output interface display page 350 may additionally and/or alternatively display a list of diagnostic procedure options, treatment options, and the like.

In a step 214, the healthcare provider (HCP) may select a medication to prescribe to the patient from a medication list. For example, after selecting a medication 356 of the medication list 354, a button or other icon may appear which may be configured to indicate that the selected medication is to be prescribed or otherwise moved forward in the prior authorization process. By way of another example, a user may be able to "double click" a medication 356 in order to select the medication 356 to move forward with the prior authorization process.

In a step 216, it is determined whether prior authorization is required for the selected medication. It is contemplated herein that step 216 may be carried out by the one or more processors 108 of the healthcare provider device 102 and/or the one or more processors 118 of the server 116. For example, the one or more processors 118 may be configured to access a database of medications stored in memory 110 which require prior authorization. By way of another example, the one or more processors 108 may be configured to analyze one or more insurance provider prior authorization rules to determine if the selected medication requires prior authorization. By way of another example, the one or more processors 118 of server 116 may be configured to access one or more databases 122 or prior authorization rules stored in memory 120 in order to determine whether the selected medication requires prior authorization. The one or more processors 118 may then be further configured to transmit one or more signals to healthcare provider device 102 via network 114 which indicate whether prior authorization is required.

If it is determined that prior authorization is not required for the selected medication in step 216, method 200 may proceed to step 217 and 218. In step 217, the healthcare provider may be informed that prior authorization is not required via the healthcare provider device 102. In step 218, a medication request claim is transmitted to a pharmacy. It is contemplated herein that a medication request claim may be submitted to a pharmacy electronically via the healthcare provider device 102. For example, an output interface display screen may include a button or other icon which may be selected to electronically transmit the medication request claim. In other embodiments, a medication request claim may be printed off such that the patient may physically deliver the paper-based medication request claim to a pharmacy. It is further noted herein that an output interface display screen configured to electronically transmit the medication request claim may additionally include a button, check-box, or other input box configured to receive an indication of patient consent to share and/or transmit health information input into the healthcare provider device 102.

Conversely, if it is determined that prior authorization is required for the selected medication in step 216, method 200 may proceed to step 220. In step 220, a prior authorization form for the selected medication is retrieved and displayed by the healthcare provider device. In embodiments, a database of prior authorization forms for various medications may be maintained in memory 110 of healthcare provider device 102. In this embodiment, the one or more processors 108 may be configured to retrieve the appropriate prior authorization form from memory 110 and display the prior authorization form. In other embodiments, the one or more processors 108 may be configured to transmit one or more signals to server 116 via network 114, wherein the one or more signals are configured to cause the one or more processors 118 of server 116 to retrieve the appropriate prior authorization form from the one or more databases 122 maintained in memory 120. The one or more processors 118 may then be configured to transmit the appropriate prior authorization form to the healthcare provider device 102 via network 114.

In a step 222, the prior authorization form displayed on healthcare provider device 102 may be auto-populated, and a user (e.g., patient, HCP, or the like) may be prompted to complete the prior authorization form. For example, FIG. 3G illustrates an output interface display page 360 of a GUI 106 generated at a display 104 of a healthcare provider device 102 depicting a prior authorization form, in accordance with one or more embodiments of the present disclosure. To the extent applicable, description associated with structures illustrated in FIGS. 3A-3F may be regarded as applying to structures illustrated in FIG. 3G, unless noted otherwise herein.

As shown in FIG. 3G, output interface display page 360 may include a prior authorization form 362 including one or more user input fields 364a, 364b, 364c, 364d, 364e, 364n. It is noted herein that the prior authorization form 362 may include a real prior authorization form which is displayed on the output interface display page 360. In this regard, the prior authorization form 362 may include an image of a PDF, a scanned image, and the like. Furthermore, the input fields 364a-364n may include input fields which are superimposed over relevant portions of the prior authorization form 362 image. The one or more user input fields 364a, 364b, 364c, 364d, 364e, 364n may include, but are not limited to, plain text input boxes, auto-fill input text boxes, drop-down input boxes, drop-down selectable/searchable lists, or the like. As noted previously, one or more of the user input fields 364a, 364b, 364c, 364d, 364e, 364n may be auto-populated. For example, the one or more processors 108 may be configured to cross-reference the user input fields 364a, 364b, 364c, 364d, 364e with information inputted by the user in input interface display screens 300, 310, 320, 330, 340 and auto-fill any user input fields 364a, 364b, 364c, 364d, 364e which request information that has been previously input. For instance, if user input field 364a (e.g., User Input Field #1 364a) included an input field requesting the name of the patient, the one or more processors 108 may be configured to auto-fill the user input field 364a with the information received by the one or more input boxes 308 illustrated in FIG. 3A.

The one or more processors 108 may be further configured to prompt a user to complete the prior authorization form 362 by completing the user input fields 364 which were not auto-filled. For example, the one or more processors 108 may be configured to draw a user's attention to un-auto-filled user input fields 346 by displaying a message (e.g., text box, icon, or the like) on display 104, highlighting un-auto-filled user input fields 346, or the like.

In embodiments, a healthcare provider (HCP) may be able to attach supporting documents to the prior authorization form 362. For example, output interface display page 360 may include a button 366 configured to attach patient medical records and a button 368 configured to attach support documents for off-label prescribing. A healthcare provider may desire to attach supporting documents (e.g., patient medical records, off-label prescribing documents, or the like) in cases where the healthcare provider may be departing from the regular practices of the selected medication requiring prior authorization. For example, supporting documents may be attached to show that the patient requires a stronger medication dose than would otherwise be prescribed and/or approved. By way of another example, supporting documents may be attached to demonstrate a cause and/or need for exceeding medication quantity limits. By way of another example, supporting documents may be attached to explain off-label prescribing practices. By way of another example, supporting documents may be attached which serve to meet prior authorization requirements. In some embodiments, the database will include support documents that can be included with the prior authorization request for such purposes, and the system can be configured to allow users to add such documents to the database. Accordingly, it is contemplated herein that the ability to attach supporting documents may streamline the prior authorization process and increase the probability that prior authorization will be obtained.

In a step 224, the completed prior authorization form is transmitted to an insurance provider and/or primary benefit manager (PBM) via the healthcare provider device 102. For example, as shown in FIG. 3G, output interface display screen 360 may include a button 372 configured to submit the completed prior authorization form 362 and supporting documents (e.g., patient medical records, off-label prescribing documents, or the like). The completed prior authorization form may be time-stamped at the time of transmittal. In an additional and/or alternative embodiment, the completed prior authorization form and supporting documents may be manually delivered to the insurance provider and/or primary benefit manager (PBM) (e.g., faxed, hand-delivered, and the like).

In a step 226, as shown in FIG. 2B, the pharmacy runs the medication request claim. In a step 228, the patient may go to the pharmacy to retrieve the prescribed medication. In a step 230, the pharmacy determines whether the medication request claim is approved. The approval of the medication request claim in step 230 may be dependent on whether the prior authorization request form has been approved by the insurance provider and/or PBM. Step 230 may also include informing the patient and/or healthcare provider (e.g., via email, text, or the like) if the medication request claim is approved. For example, the healthcare provider device 102 may be configured to display one or more messages indicating that the medication request claim was approved or denied. If the claim is approved in step 230, the method 200 proceeds to step 232. In step 232, the claim is paid and the prescribed medication is provided to the patient.

If the claim is denied in step 230, the method 200 proceeds to step 234. In step 234, the medication request claim is denied. In step 236, the patient may be given the option to connect with a concierge service to assist the patient with the claim approval and/or prior authorization process.

In a step 238, information which may assist with the claim approval and/or prior authorization process may be input into the healthcare provider device 102. For example, an input interface display page may include one or more input boxes configured to receive information which may be beneficial to the claim approval and/or prior authorization process.

In a step 240, medication approval is again requested form the insurance provider and/or the PBM. In a step 242, it is determined whether the claim is approved. If the claim is approved, the method 200 proceeds to step 232, where the claim is paid and the medication is provided to the patient. In embodiments, upon approval of the claim in step 230 and/or step 242, the healthcare provider device 102 may be configured to transmit the approved claim to Electronic Health Records (EHR). If the claim is denied in step 242, the method 200 proceeds to step 244 where the patient, insurance provider, and/or PBM are notified of the denied claim.

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including, but not limited to" the term "having" should be interpreted as "having at least," the term "includes" should be interpreted as "includes, but is not limited to"). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Although the technology has been described with reference to the embodiments illustrated in the attached drawing figures, equivalents may be employed and substitutions made herein without departing from the scope of the technology as recited in the claims. Components illustrated and described herein are merely examples of devices and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed:

1. A healthcare provider device, comprising:
    a display coupled to one or more processors, the display including a graphical user interface generated by the one or more processors, the graphical user interface comprising:
        one or more input interface display pages, including:
            one or more input boxes configured to receive physiological information associated with a patient;
            one or more input boxes configured to receive insurance provider information of the patient;
            one or more input fields configured to receive one or more attachments including patient medical records and documentary evidence in support of an off-label prescription, wherein the one or more input fields include a first button configured to attach the patient medical records and a second button configured to attach supportive documents justifying use of a specific medication or other treatment modality;
            one or more drop-down menus for selecting one or more historical medications used by the patient; and
            an input box configured to receive a medical diagnosis of the patient from a healthcare provider, or extracted from an electronic health record;
            one or more input boxes configured to receive past treatment information of the patient to assess whether step therapy requirements are met, the one or more input boxes including:
                an input box configured to receive a name of a past medication;
                an input box configured to receive a strength of the past medication;
                an input box configured to receive a form of the past medication;
                one or more input boxes configured to receive a date range for use of the past medication; and
                an input box configured to receive information associated with a reason for stopping the past medication; and
        one or more output interface display pages, including:
            a medication list with one or more medication options generated based at least on the received medical diagnosis, insurance provider formulary rules, past treatment information of the patient and insurance-specific step therapy requirements, physiological information, and one or more historical medications;
            a prior authorization form for a prior authorization request, the prior authorization form including one or more input boxes configured to receive one or more prior authorization input fields, wherein the prior authorization form further includes one or more buttons configured to receive a user command, the one or more buttons configured to cause the one or more processors to transmit the prior authorization form with the one or more attachments including the documentary evidence in support of the off-label prescription to at least one of an insurance provider or a pharmacy benefit manager.

2. The healthcare provider device of claim 1, wherein the prior authorization form further includes one or more buttons configured to receive a user command, the one or more buttons configured to cause the one or more processors to transmit the prior authorization form to at least one of an insurance provider or a pharmacy benefit manager.

3. The healthcare provider device of claim 1, wherein the one or more input boxes for receiving physiological information associated with the patient include:
    an input box configured to receive a name of the patient;
    an input box configured to receive a height of the patient;
    an input box configured to receive a weight of the patient; and
    an input box configured to receive a date-of-birth of the patient.

4. The healthcare provider device of claim 1, wherein the one or more input interface display pages further include one or more drop-down menus with one or more selectable predictive text options for one or more prescription allergies of the patient.

5. The healthcare provider device of claim 1, wherein the one or more input interface display pages further include one or more input boxes configured to receive biologic information of the patient.

6. The healthcare provider device of claim 1, wherein the one or more input interface display pages further include at least one button configured to add one or more drop-down menus with selections for one or more historical medication prescriptions of the patient.

7. The healthcare provider device of claim 1, wherein the one or more medication options include one or more medications that are likely to be approved by an insurance provider for the patient based on one or more prior authorization rules of the insurance provider.

8. The healthcare provider device of claim 1, wherein the medication list is sorted based on at least one of medication cost, patient ratings, provider ratings, availability, and genetic profile.

9. The healthcare provider device of claim 1, wherein the one or more drop-down menus for selecting one or more historical medication prescriptions of the patient are generated based on one or more prescription drug monitoring program databases.

10. The healthcare provider device of claim 1, wherein the one or more output interface display pages further include one or more text boxes conveying medication information associated with the one or more medication options of the medication list.

11. The healthcare provider device of claim 1, wherein the one or more input interface display pages further include one or more buttons configured to toggle between pages of the one or more input interface display pages.

12. The healthcare provider device of claim 1, wherein the one or more output interface display pages further include one or more buttons configured to toggle between pages of the one or more output interface display pages.

13. The healthcare provider device of claim 1, wherein the one or more input boxes configured to receive insurance provider information of the patient include:
an input box configured to receive a name of an insurance provider;
an input box configured to receive a policy number;
an input box configured to receive a member ID number; and
an input box configured to receive a BIN number.

14. The healthcare provider device of claim 1, wherein the input box configured to receive a medical diagnosis of the patient includes a searchable drop-down list of ICD-10 diagnosis codes.

15. A healthcare provider device, comprising:
a display coupled to one or more processors, the display including a graphical user interface generated by the one or more processors, the graphical user interface comprising:
one or more input interface display pages, including:
one or more input boxes configured to receive physiological information associated with a patient;
one or more input boxes configured to receive insurance provider information and pharmacy benefit manager information of the patient;
one or more input fields configured to receive one or more attachments including patient medical records and documentary evidence in support of a treatment, wherein the one or more input fields include a first button configured to attach the patient medical records and a second button configured to attach documents in support of the treatment;
one or more drop-down menus for selecting one or more historical medications used by the patient; and
an input box configured to receive a medical diagnosis of the patient;
one or more input boxes configured to receive past treatment information of the patient to assess whether step therapy requirements are met, the one or more input boxes including:
an input box configured to receive a name of a past medication;
an input box configured to receive a strength of the past medication;
an input box configured to receive a form of the past medication;
one or more input boxes configured to receive a date range for use of the past medication; and
an input box configured to receive information associated with a reason for stopping the past medication; and
one or more output interface display pages, including:
a medication list with one or more medication options generated based at least on the received medical diagnosis, insurance provider formulary rules, past treatment information of the patient and insurance-specific step therapy requirements, physiological information, patient biologic information including pharmacogenetic information of the patient, and one or more historical medications, wherein medication characteristics are noted including medications which the patient has previously tried, medications which are known to require prior authorization and meet criteria, medications which are known to require prior authorization and do not meet criteria, medications which do not require prior authorization, medications which are excluded from a formulary and medications which may cause allergic reactions based on inputted allergy information, and wherein the selection of a medication from the medication list launches a separate output interface display page including a text box with detailed information regarding the selected medication, wherein the detailed information includes: brand names, generic names, dose, form, quantity, method of administration, indication, side-effects, mechanisms of action, pharmacokinetics, medication interactions, black box warnings, monitoring requirements, and dietary effects;
a drop-down menu configured to provide options for sorting the medication list based on one or more factors, including: medication cost, probability of approval by an insurance provider, patient preference, patient ratings, insurance provider tier or preference, availability at a preferred pharmacy of the patient, and appropriateness based on pharmacogenetic information of the patient;
a prior authorization form for a prior authorization request, the prior authorization form including one or more input boxes configured to receive one or more prior authorization input fields, wherein the prior authorization form further includes one or more buttons configured to receive a user command, the one or more buttons configured to cause the one or more processors to transmit the prior authorization form with the one or more attachments including the documentary evidence in support of the treatment to at least one of the insurance provider or a pharmacy benefit manager.

16. A healthcare provider device, comprising:

a display coupled to one or more processors, the display including a graphical user interface generated by the one or more processors, the graphical user interface comprising:

one or more input interface display pages, including:

one or more input boxes configured to receive physiological information associated with a patient;

one or more input boxes configured to receive insurance provider information of the patient;

one or more input fields configured to receive one or more attachments including patient medical records and documentary evidence in support of an off-label prescription, wherein the one or more input fields include a first button configured to attach the patient medical records and a second button configured to attach supportive documents for off-label prescribing;

one or more drop-down menus for selecting one or more historical medications used by the patient; and an input box configured to receive a medical diagnosis of the patient from a healthcare provider;

one or more input boxes configured to receive past treatment information of the patient to assess whether step therapy requirements are met, the one or more input boxes including:

an input box configured to receive a name of a past medication;

an input box configured to receive a strength of the past medication;

an input box configured to receive a form of the past medication;

one or more input boxes configured to receive a date range for use of the past medication; and an input box configured to receive information associated with a reason for stopping the past medication; and one or more output interface display pages, including:

a medication list with one or more medication options generated based at least on the received medical diagnosis, insurance provider formulary rules, past treatment information of the patient and insurance-specific step therapy requirements, physiological information, patient biologic information including genetic profile information of the patient, and one or more historical medications, wherein medication characteristics are noted including medications which the patient has previously tried, medications which are known to require prior authorization, and medications which may cause allergic reactions based on inputted allergy information, and wherein the selection of a medication from the medication list launches a separate output interface display page including a text box with detailed information regarding the selected medication, wherein the detailed information includes: scientific or generic names, prescribing practices, primary purposes, side-effects, mechanisms of action, pharmacokinetics, medication interactions, black box warnings, monitoring requirements, and dietary effects;

a drop-down menu configured to provide options for sorting the medication list based on one or more factors, including: medication cost, probability of approval by the insurance provider, patient preferences, patient ratings, insurance provider preferences, insurance provider ratings, availability, and genetic profile information of the patient;

a prior authorization form for a prior authorization request, the prior authorization form including one or more input boxes configured to receive one or more prior authorization input fields, wherein the prior authorization form further includes one or more buttons configured to receive a user command, the one or more buttons configured to cause the one or more processors to transmit the prior authorization form with the one or more attachments including the documentary evidence in support of the off-label prescription to at least one of an insurance provider or a pharmacy benefit manager.

* * * * *